Figure 1:
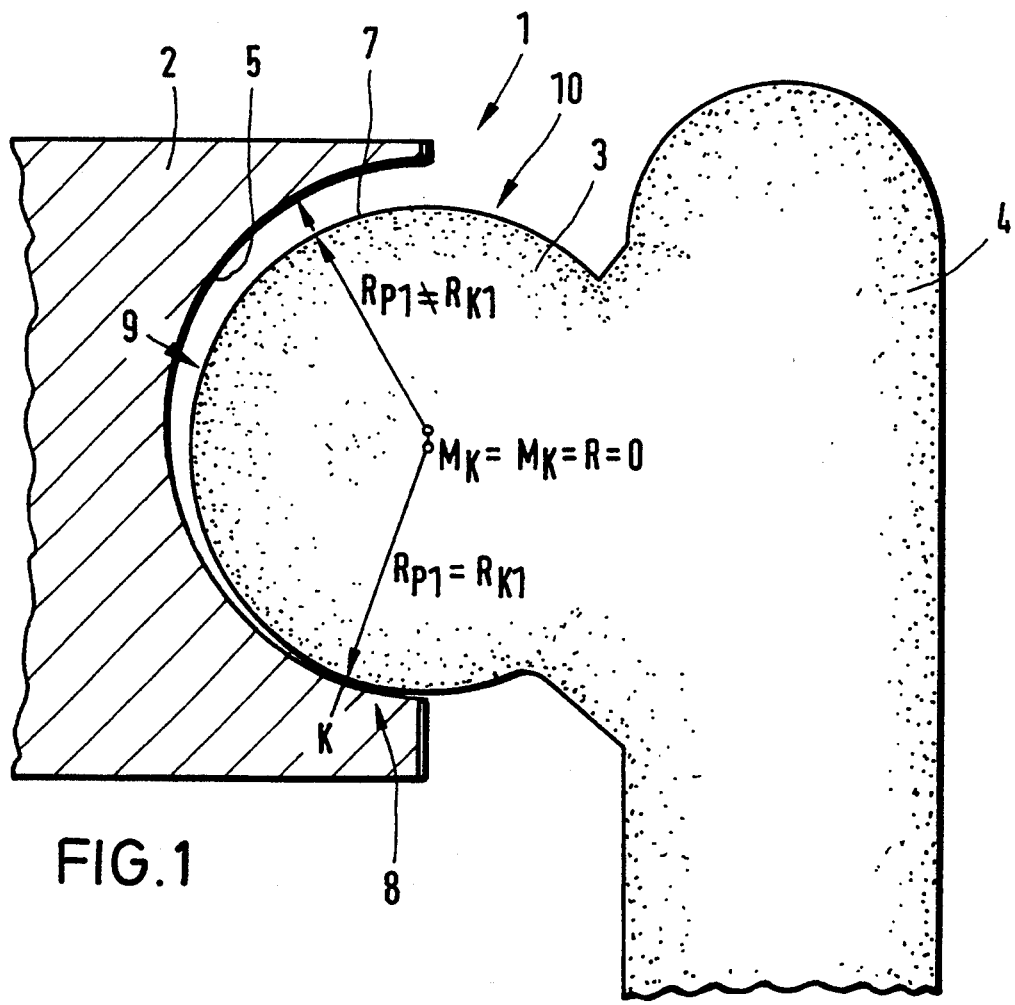

United States Patent [19]

Kubein-Meesenburg et al.

[11] Patent Number: 5,383,936
[45] Date of Patent: Jan. 24, 1995

[54] ARTIFICIAL JOINT AS AN ENDOPROSTHESIS FOR THE HUMAN SHOULDER JOINT

[75] Inventors: Dietmar Kubein-Meesenburg, Kreiensen; Hans Nägerl, Gleichen/OT, both of Germany

[73] Assignee: Joachim Theusner, Munich, Germany

[21] Appl. No.: 126,912

[22] Filed: Sep. 24, 1993

[30] Foreign Application Priority Data

Sep. 26, 1992 [DE] Germany .............................. 4232313

[51] Int. Cl.$^6$ .............................................. A61F 2/40
[52] U.S. Cl. ........................................ 623/19; 623/18
[58] Field of Search ................... 623/16, 18, 19, 22, 623/23

[56] References Cited

U.S. PATENT DOCUMENTS

| | | | |
|---|---|---|---|
| 4,024,588 | 5/1977 | Janssen et al. | 623/22 |
| 4,031,570 | 6/1977 | Frey | 623/22 |
| 4,159,544 | 7/1979 | Termanini | 623/22 |
| 4,261,062 | 4/1981 | Amstutz . | |
| 4,550,450 | 11/1985 | Kinnett . | |
| 4,666,448 | 5/1987 | Ganz | 623/22 |
| 4,784,662 | 11/1988 | Muller | 623/22 |
| 4,911,723 | 3/1990 | Menschik | 623/22 |
| 4,919,675 | 4/1990 | Dietschi | 623/22 |
| 4,964,865 | 10/1990 | Burkhead . | |
| 5,032,132 | 7/1991 | Matsen, III . | |

FOREIGN PATENT DOCUMENTS

0360734 7/1989 European Pat. Off. .
2541890 3/1983 France .
WO90/11062 10/1990 WIPO .

*Primary Examiner*—David Isabella
*Attorney, Agent, or Firm*—Jones & Askew

[57] ABSTRACT

The invention at hand concerns an artificial joint, in particular an endoprosthesis for a human shoulder joint, consisting of two parts, a joint head (3) and a joint pan (2) with spherical joint surfaces moving relative to one another. The bending conditions of the functional surfaces (5,7) are convex-concave in the frontal plane as well as in the perpendicular transverse plane. The joint geometry of the functional surfaces towards each other in both planes is determined through a dimeric joint chain which runs through the rotation centers of the functional surfaces of each of the intersection contours. The joint head (3) and the joint pan (2) are arranged in relation to their functional surfaces such that in their position corresponding to the rest position of the arm in a dangling state the functional surfaces (5,7) have the same radius of curvature in the contact area (8) on both sides in the frontal plane with a linear contact of the functional surfaces (5,7), and such that a roll-off area (9) adjoins, in which the radii $R_{P1}$, $R_{K1}$ of both functional surfaces (5,7) are selected such that a circumferentially widening gap section covers the area between both joint parts (2,3).

13 Claims, 2 Drawing Sheets

ARTIFICIAL JOINT AS AN ENDOPROSTHESIS FOR THE HUMAN SHOULDER JOINT

The present invention relates to an artificial joint, in particular an endoprosthesis for the human shoulder joint.

It has generally been the assumption that the shoulder blade is one of the simple joint constructions and can be viewed as a ball joint, whereby this ball joint is granted three degrees of rotational freedom.

Furthermore, it is already known from U.S. application Ser. No. 08/609,439 filed Jan. 26, 1993 that artificial joints for use in the human body with two joint parts with spherical functional surfaces moving relative to one another have curvature properties on their functional surfaces; for instance, a convex-concave configuration of the functional surface, such that a joint geometry is present which is determined by a joint chain with two joint axes; this joint chain is called a dimeric joint chain. Here the axes of rotation of both functional surfaces can be located within the joint part with the convex functional surface so that a stable joint chain results. The precondition for the functioning of this dimeric joint chains is the presence of a frictional connection in the point of contact of the two functional areas.

The goal of the present invention is to improve the heretofore familiar endoprostheses for the human shoulder that are all built under the principle of the ball joint, using the knowledge of the functional method of the dimeric joint chain, in such a way that an endoprosthesis is created that matches the natural joint function as well as possible.

According to the invention, this is fulfilled with an artificial joint consisting of two joint parts moving relative to one another, a joint head, and a joint pan, with a ball shaped joint surface whereby the curvature conditions of the functional surfaces are convex-concave in their frontal plane (vertical plane) as well as perpendicular transverse plane, and the joint geometry of the functional surfaces is determined on both planes by a dimeric joint chain that runs through the rotation centers of the functional surfaces of the respective sectional contours, whereby the joint head and the joint pan are configured with respect to their functional surfaces in such a manner that in their position corresponding to the rest position of the arm in a hanging arm state, the two sided functional surfaces in the frontal plane have the same radius of curvature $R_{K1}=R_{P1}$ in one support area in linear contact with the functional surface, onto which a roll-off area [sic] adjoins, in which the radii of the functional surfaces are selected in such a way that a constantly widening gap section between the two joint parts results in a circumferential direction. Furthermore, in the transverse plane that runs radially through each point of contact of the functional surfaces of the joint parts, the invention proposes to dimension the functional surface radii such that a circumferentially widening gap extends on the point of contact of the functional surfaces. The joint according to the invention permits five degrees of freedom. The joint construction according to the invention is based on the recognition that the joint head on the one hand rotates around its own center of curvature at a particular angular velocity, whereby the point of contact remains steady on the joint surface of the joint pan at one point and the point of contact on the joint head moves in the opposite direction to the rotation; in addition, the joint head rotates around the midpoint of the joint pan at a particular angular velocity whereby the point of contact on the joint head remains immobile but moves in the same direction on the functional surface of the joint pan. Both rotations above overlap. Hereby, the present invention furthermore guarantees that at rest position the joint pan is loaded on its lower part such that a linear contact of the functional surface is present, wherein an optimum force input results. Furthermore, the formation of the joint gap according to the invention, which is provided by the incongruence of the bending radii of the articulating functional surfaces, results in the contact point of the functional surfaces moving upwards with the lifting of the arm so that the joint gap becomes smaller towards the upper area and larger towards the lower area. This leads to an increase in pressure of the synovial fluid in the upper joint gap and a decrease in pressure in the lower area. In addition to this, the point of the joint surfaces of the joint head that momentarily forms the point of contact, despite the upward moving of the point of contact, has a velocity V directed downwards and can take with it the synovial fluid. In this way, the joint according to the invention works on the principle of a rotary pump.

Further advantageous designs are contained in the subclaims.

The invention is described further according to the embodiment presented in the attached diagrams.

They show

Figure 2:
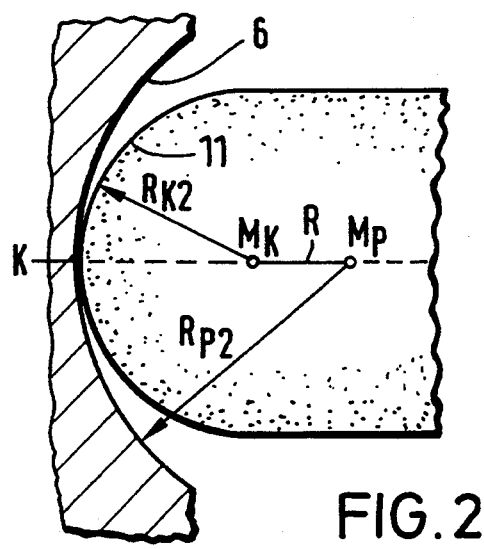
Figure 3:
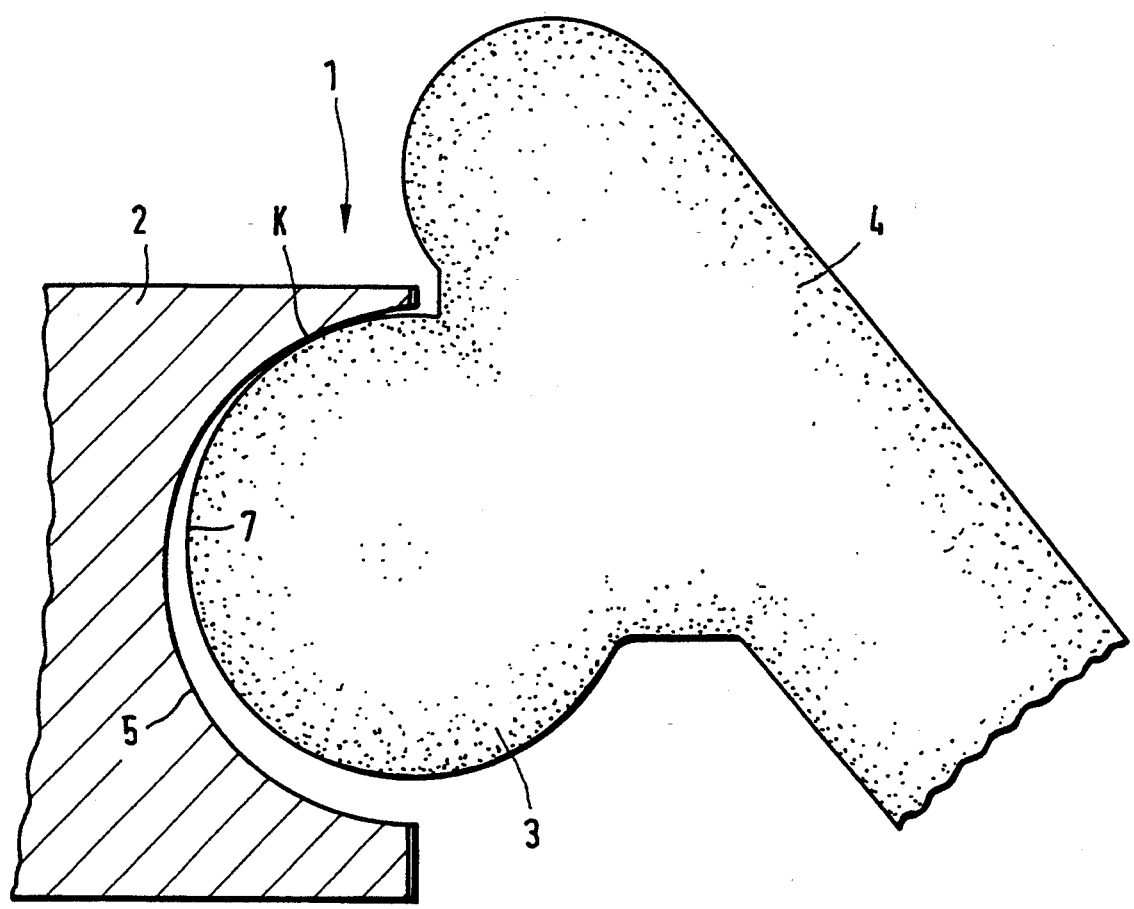

FIG. 1 a front section of a joint according to the invention,

FIG. 2 a cross section to the representation of the section in FIG. 1 in a radial direction through the contact point of the functional surface of the joint parts, FIG. 3 a front section a joint according to the invention in a lifted position of the arm.

FIG. 1 represents an artificial joint 1 according to the invention for the replacement of the human shoulder joint. This artificial joint 1 is made of a joint pan 2 and a joint head 3. The joint head 3 is connected with the upper arm bone 4. The joint pan 2 has a convex curvature with the radius of curvature $R_{P1}$ in the frontal plane, whereby the functional plane 5 formed in this manner is circular, that is the bend $R_{P1}$ is constant over the entire functional surface area. It has a practical value of about 25 mm. It is discernible from FIG. 2 that, in the transverse plane perpendicular to the frontal plane according to FIG. 1, the joint pan 2 has a functional surface 6 that actually has a constant radius of curvature $R_{P2}$ over the entire area of the functional surface 6. It is additionally provided here that both radii of curvature of the functional surfaces 5 and 6 are equal, that is $R_{P1}=R_{P2}$. The joint head 3 has a spherical surface, whereby the radius of curvature $R_{K1}$ of the functional surface 7 is not constant in the front section plane. Instead, the radius of curvature $R_{K1}$ is measured in such a way that, in the rest position of the joint according to the invention as represented in FIG. 1, which corresponds to the position of the human joint with a dangling arm, the joint head 3 has a radius of curvature in the lower area of the joint pan 2 within the contact area 8 that corresponds to the radius of curvature $R_{P1}$ of the joint pan 2. Thereby, a linear contact between both functional surfaces 5,7 is produced by joint head 3 and joint pan 2 in this contact area 8. This linear contact area 8 can have a value of about 20° on the joint head 3 with respect to the circumference. An roll-off area 9 adjoins this linear contact area 8 in which the radii of the functional surfaces 5,7 of joint pan 2 and joint head 3 are configured such that a constantly widening gap section results between both joint parts 2,3 in the direction of the circumference. This widening gap section is caused in the design example shown by the constant decrease of the radius of the functional surface 7 of the joint head 3, starting from the radius within the contact area 8. The suitable value of this decrease of the radius is a maximum of 20% of the radius of the functional surfaces of the joint head 3 and the joint pan 2 within the contact area 8. The roll-off area 9 suitably covers a circumference area of the joint head of about 190°. Furthermore, it is provided according to the invention that an end area 10 with a constant radius difference of the functional surfaces of joint head 3 and joint pan 2 adjoins the roll-off area 9 in circumferential direction; the end area has a value of about 40°–70° of the circumference of the joint head 3. It is discernible in FIG. 2 that in the transverse plane that runs radially through each contact point K of the functional surfaces of the joint parts 2,3, the radii of the functional surfaces 6,11 are measured in such a way that on both sides of the contact point K a circumferentially widening gap results. The radius $R_{P2}$ of the functional surface 6 of the joint pan 2 has the same radius as on the functional surface 5 in the frontal plane. However, the radius $R_{K2}$ of the functional surface 11 of the joint head 3 is formed differently from the radius of the functional surface 7 of the joint head in the frontal plane. Here it is suitable that the radius difference of both functional surfaces 6,11 have a maximum value of 30% of the radius of the functional surfaces in the contact area 8 on both sides of the contact point K. It is likewise discernible here that the radius $R_{K2}$ of the joint head 3 is around 12% smaller than the radius of the radially equal functional surfaces in the contact area 8. The radius $R_{K2}$ has a suitable value of about 22 mm. The radius $R_{K2}$ of the functional surface of the joint head in the transverse plane is reduced here from the maximum value in contact point in a dorsal direction by about 3 mm over a circumferential angle of about 90°, and in a ventral direction over a circumferential angle of 90°, it is reduced by a maximum of 1 mm.

As a result of the position of midpoints $M_K$ and $M_P$ of the functional surfaces in the frontal plane as well as in the transverse plane, the subject of the example at hand are joint parts 2 and 3 moving relative to one another with a convex concave formation of the functional surfaces 5,7 or 6,11, whereby the midpoints of the functional surfaces $M_K$ and $M_P$ each lie in the joint part with the convex functional surface 7,11, namely the joint head 3, and whereby the condition is met that a dimeric stable joint chain is formed, whereby the chain link R has a joint axis path with the radius $R=R_P-R_K$, whereby this value is larger than zero or, in the area of the linear shaped contact, is equal to zero. In FIG. 3 the position of the joint 1 according to the invention is represented at a lifted arm position at 60°.

In the preceding it is provided that the joint pan has constant and equal radii of the functional surfaces in both section planes and that the radii of the functional surfaces of the joint head vary. It lies also within the scope of the invention that the radii of the functional surfaces of the joint head are constant and equal and that the radii of the functional surfaces of the joint pan vary, such that the geometries of the functional surfaces according to the invention result.

We claim:

1. An artificial joint for the human shoulder joint and including two joint parts, a joint head and a joint pan, moving relative to one another with spherical functional joint surfaces (6, 11) associated with the joint parts, whereby the curvatures of the functional surfaces are convex-concave in a plane frontal to the functional surfaces as well as in a plane perpendicular to the frontal plane, and the geometry of the joint planes with respect to each other is determined in both planes by a dimeric joint chain that runs through the rotational centers of the functional surfaces of each intersection contour, characterized in that the joint head (3) and the joint pan (2) are formed in relation to their functional surfaces in such a way that in their position corresponding to the rest position of the human joint in a dangling state, the mutual frictional surfaces (5, 7) have the same radius of curvature in the frontal plane within a contact area (8) and produce a linear contact of the functional surfaces (5, 7);

a roll-off area (9) adjoins said surface areas in which the radii $R_{P1}$, $R_{K1}$ of the two functional surfaces (5, 7) are operative to produce a circumferentially widening gap section occupying the area between the joint parts (2, 3); and in the transverse plane running radially through each contact point K of the functional surfaces (6, 11) of the joint parts (2, 3), the radii ($R_{P2}$, $R_{K2}$) of the functional surfaces (6, 11) are dimensioned to produce a circumferentially widening gap on each side of the contact point K.

2. An artificial joint according to claim 1, characterized in the roll-off area (9) covers a circumferential area of about 180° around the joint head.

3. An artificial joint according to claim 1, characterized in that the contact area (8) covers a circumferential area of about 20° around the joint head (3).

4. An artificial joint according to claim 1, characterized in that an end area (10) with a constant radius difference between the functional surfaces (5, 7) is attached to the roll-off area (9) in a circumferential direction.

5. An artificial joint according to claim 4 characterized in that the end area (10) covers an angular area of about 70°.

6. An artificial joint according to claim 1, characterized in that the radius difference in the roll-off area (9) has a maximum value of 20% of the radius of both function areas (5, 7) in the contact area (8).

7. An artificial joint according to claim 1, characterized in that the radius difference of the functional surfaces (6, 11) has a maximum value on both sides of a contact point (K) of 30% of the radius of the functional surfaces (5, 7) in the contact area (8).

8. An artificial joint according to claim 1, characterized in that the functional surfaces (5, 7), (6, 11) of one of the joint parts (2, 3) are circular in the frontal plane as well as in the transverse plane and have the same radius, which corresponds to the radius to the functional surfaces (5, 7) in the contact area (8).

9. An artificial joint according to claim 8 characterized in that the joint part with the equi radial functional surfaces (5,6) is the joint pan (2).

10. An artificial joint according to claim 8, characterized in that the radius of the equiradial functional surfaces (5, 6) has a value of about 25 mm.

11. An artificial joint according to claim 13 characterized in that the radius $R_{K2}$ of the joint head (3) is reduced, starting from its maximum value as seen in the transverse plane, by about 3 mm over a circumferential angle of 90° in the dorsal direction, and by a maximum of 1 mm in the ventral direction over a circumferential angle of 90°.

12. An artificial joint for the human shoulder joint and including two joint parts, a joint head and a joint pan, moving relative to one another with spherical functional joint surfaces (6, 11) associated with the joint parts, whereby the curvatures of the functional surfaces are convex-concave in a plane frontal to the functional surfaces as well as in a plane perpendicular to the frontal plane, and the geometry of the joint planes with respect to each other is determined in both planes by a dimeric joint chain that runs through the rotational centers of the functional surfaces of each intersection contour, characterized in that the joint head (3) and the joint pan (2) are formed in relation to their functional surfaces in such a way that in their position corresponding to the rest position of the human joint in a dangling state, the mutual functional surfaces (5, 7) have the same radius of curvature in the frontal plane within a contact area (8) and produce a linear contact of the functional surfaces (5, 7);

a roll-off area (9) adjoins said surface areas in which the radii $R_{P1}$, $R_{K1}$ of the two functional surfaces (5, 7) are operative to produce a circumferentially widening gap section occupying the area between the joint pans (2, 3);

the functional surfaces (5, 7), (6, 11) of the joint pan are circular in the frontal plane as well as in the transverse plane and have the same radius, which corresponds to the radius to the functional surfaces (5, 7) in the contact area (8); and in the frontal plane, the radius of the joint head (3), starting from the contact area (8), is reduced from about 25 mm to about 21 mm at the end of the roll-off area (9).

13. An artificial joint for the human shoulder joint and including two joint parts, a joint head and a joint pan, moving relative to one another with spherical functional joint surfaces (6, 11) associated with the joint parts, whereby the curvatures of the functional surfaces are convex-concave in a plane frontal to the functional surfaces as well as in a plane perpendicular to the frontal plane, and the geometry of the joint planes with respect to each other is determined in both planes by a dimeric joint chain that runs through the rotational centers of the functional surfaces of each intersection contour, characterized in that the joint head (3) and the joint pan (2) are formed in relation to their functional surfaces in such a way that in their position corresponding to the rest position of the human joint in a dangling state, the mutual functional surfaces (5, 7) have the same radius of curvature in the frontal plane within a contact area (8) and produce a linear contact of the functional surfaces (5, 7);

a roll-off area (9) adjoins said surface areas in which the radii $R_{P1}$, $R_{K1}$ of the two functional surfaces (5, 7) are operative to produce a circumferentially widening gap section occupying the area between the joint parts (2, 3);

the functional surfaces (5, 7), (6, 11) of the joint pan are circular in the frontal plane as well as in the transverse plane and have the same radius, which corresponds to the radius to the functional surfaces (5, 7) in the contact area (8); and the radius of the joint head, as seen in the transverse plane, is about 12% smaller than the radius functional surfaces (5, 7) in the contact area (8).

* * * * *

UNITED STATES PATENT AND TRADEMARK OFFICE
CERTIFICATE OF CORRECTION

PATENT NO. : 5,383,936
DATED : January 24, 1995
INVENTOR(S) : DIETMAR KUBEIN-MEESENBURG, ET. AL.

It is certified that error appears in the above-identified patent and that said Letters Patent is hereby corrected as shown below:

Column 4, line 17, "frictional" should read --functional--.

Signed and Sealed this

Eighteenth Day of April, 1995

Attest:

BRUCE LEHMAN

Attesting Officer

Commissioner of Patents and Trademarks